United States Patent [19]

Nagase et al.

[11] Patent Number: 4,632,938
[45] Date of Patent: Dec. 30, 1986

[54] THIOPHENYLUREAS, THEIR PRODUCTION AND USE

[75] Inventors: Hiroshi Nagase, Kawanishi; Yasuo Sato, Kyoto, both of Japan

[73] Assignee: Takeda Chemical Industries, Ltd., Osaka, Japan

[21] Appl. No.: 706,297

[22] Filed: Feb. 27, 1985

[30] Foreign Application Priority Data

Feb. 27, 1984 [JP] Japan .................................. 59-36882

[51] Int. Cl.⁴ ..................... A01N 47/34; C07C 127/22
[52] U.S. Cl. ........................................ 514/594; 564/44
[58] Field of Search ...................... 564/44, 23; 514/594

[56] References Cited

U.S. PATENT DOCUMENTS

| | | | |
|---|---|---|---|
| 4,013,717 | 3/1977 | Wellinga et al. | 564/44 |
| 4,089,975 | 5/1978 | Wade et al. | 564/44 |
| 4,276,310 | 6/1981 | Sirrenberg et al. | 564/23 |
| 4,277,499 | 7/1981 | Sirrenberg et al. | 564/44 |
| 4,348,412 | 9/1982 | Ehrenfreund | 564/44 |

FOREIGN PATENT DOCUMENTS

| | | |
|---|---|---|
| 71279 | 2/1983 | European Pat. Off. |
| 2106499 | 4/1983 | United Kingdom .................. 564/44 |
| 2106500 | 4/1983 | United Kingdom .................. 564/44 |
| 2106501 | 4/1983 | United Kingdom .................. 564/44 |

Primary Examiner—Charles F. Warren
Assistant Examiner—Carolyn S. Greason
Attorney, Agent, or Firm—Wenderoth, Lind & Ponack

[57] ABSTRACT

New insecticidal or/and ovicidal benzoylurea derivatives of the formula:

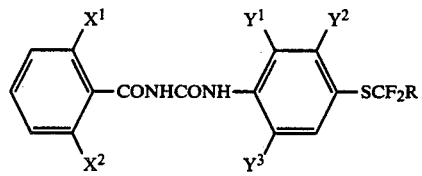

wherein $X^1$ is hydrogen or halogen; $X^2$ is halogen; $Y^1$, $Y^2$ and $Y^3$ are hydrogen, halogen or alkyl, whereby at least one of $Y^1$, $Y^2$ and $Y^3$ is other than hydrogen; and R is hydrogen or a group represented by the formula $-CF_aZ_bH_{(3-a-b)}$ wherein a and b are 0, 1, 2 or 3, with $a+b \leq 3$ and Z is halogen, their production and use.

9 Claims, No Drawings

THIOPHENYLUREAS, THEIR PRODUCTION AND USE

The present invention relates to benzoylurea derivatives of the formula:

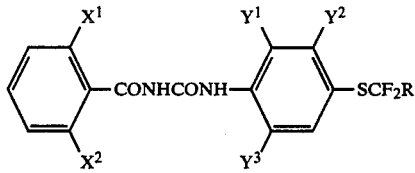

wherein $X^1$ is hydrogen or halogen; $X^2$ is halogen; $Y^1$, $Y^2$ and $Y^3$ are hydrogen, halogen or alkyl, whereby at least one of $Y^1$, $Y^2$ and $Y^3$ is other than hydrogen; and R is hydrogen or a group represented by the formula $-CF_aZ_bH_{(3-a-b)}$ wherein a and b are 0, 1, 2 or 3, with $a+b \leq 3$ and Z is halogen, which are novel compounds possessing excellent insecticidal activities. The invention also related to a process for producing the same, and to insecticides containing the same.

Some of N-(2,6-dihalogenobenzoyl)-N'-(substituted-phenyl)urea derivatives which are benzoylurea derivatives have heretofore been known to possess insecticidal activity (e.g., British Pat. Nos. 1324293 and 1501607, U.S. Pat. No. 4,277,499, European Patent Publication Nos. 71279 and 88343, etc.). However, the insecticidal effect produced by the benzoylurea derivatives which have been concretely synthesized is far from being satisfactory.

The present inventors, after extensive research and investigation into a compound exhibiting excellent insecticidal effect, succeeded in the synthesis of novel benzoylurea derivatives of the formula [I], which have not concretely been synthesized so far, through the reaction of a compound of the formula:

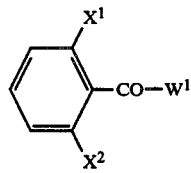

with a compound of the formula:

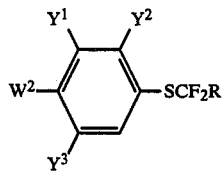

wherein $X^1$, $X^2$, $Y^1$, $Y^2$, $Y^3$ and R are as defined hereinbefore; and one of $W^1$ and $W^2$ is $-N{=}C{=}O$ (isocyanato) and the other is amino. The inventors found that these compounds [I] unexpectedly exhibit insecticidal (particularly, molt inhibitory) and ovicidal activities superior to those of known compounds having analogous structure thereto and also are of lessened toxicities toward mammals and fishes, thus finding application as a safe insecticide exerting less adverse effects on the environment.

Thus, the present invention relates to:
(1) Benzoylurea derivatives [I],
(2) A process for producing the benzoylurea derivatives [I], which comprises reacting a compound of the formula:

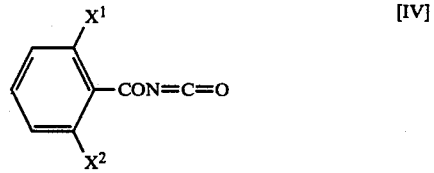

wherein $X^1$ and $X^2$ are as defined hereinbefore, with a compound of the formula:

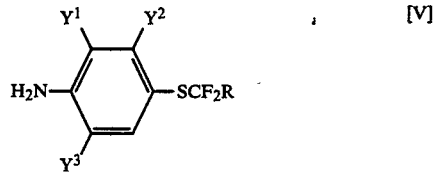

wherein $Y^1$, $Y^2$, $Y^3$ and R are as defined hereinbefore,
(3) A process for producing the benzoylurea derivatives [I], which comprises reacting a compound of the formula:

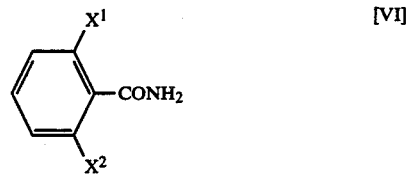

wherein $X^1$ and $X^2$ are as defined hereinbefore, with a compound of the formula:

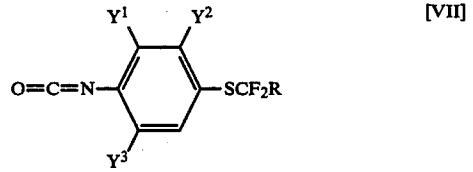

wherein $Y^1$, $Y^2$, $Y^3$ and R are as defined hereinbefore, and (4) Insecticidal compositions characteristically featured by containing the benzoylurea derivative [I].

In the above formulae, $X^1$ is hydrogen or halogen. As the halogen represented by $X^1$, there are used, for example, Cl, Br, F and I. Preferable examples of $X^1$ include, for example, hydrogen, Cl or F. $X^2$ is halogen. As the halogen represented by $X^2$, there are used those as mentioned for $X^1$. Preferable examples of $X^2$ include, for example, Cl and F. $Y^1$, $Y^2$ and $Y^3$ are hydrogen, halogen or alkyl, whereby at least one of $Y^1$, $Y^2$ and $Y^3$ is other than hydrogen. As the halogen represented by $Y^1$, $Y^2$ and $Y^3$, there are used, for example, those as mentioned for the above $X^1$. As the alkyl represented by $Y^1$, $Y^2$ and $Y^3$, there are used, for example, straight-chain or branched chain lower alkyl of 1 to 4 carbon atoms, such as methyl, ethyl, propyl, isopropyl, butyl, isobutyl, sec-butyl and t-butyl. Preferable examples of $Y^1$, $Y^2$ and $Y^3$ include, for example, hydrogen, Cl, F and methyl. R is hydrogen or a group represented by the formula —C-$F_aZ_bH_{(3-a-b)}$ wherein a and b are 0, 1, 2 or 3, with $a+b \leq 3$ and Z is halogen. As the halogen represented by Z, there are used, for example, those as mentioned for $X^1$. In the case of b being not less than 2, the halogen represented by Z may be the same or different. As concrete examples of the group represented by the formula —$CF_aZ_bH_{(3-a-b)}$, there are used, for example, $CF_3$, $CCl_3$, $CBr_3$, $CI_3$, $CF_2Cl$, $CF_2Br$, $CFCl_2$, $CFI_2$, $CFBr_2$, $CFClBr$, $CCl_2Br$, $CClBr_2$, $CHF_2$, $CHFCl$, $CHFBr$, $CHClBr$, $CHCl_2$, $CH_2F$, $CH_2Cl$, $CH_2Br$ and $CH_3$. Preferable examples of R include, for example, $CF_3$, $CHF_2$, $CHFCl$, $CHFBr$ and $CHCl_2$.

Preferable examples of the benzoylurea derivatives [I] or the object products of the present invention include, for example, compounds represented by the formula:

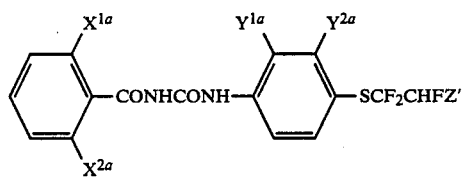

wherein $X^{1a}$ is F or Cl; $X^{2a}$ is F or Cl in the case of $X^{1a}$ being F, or hydrogen or Cl in the case of $X^{1a}$ being Cl; $Y^{1a}$ is Br, Cl, F or methyl; $Y^{2a}$ is hydrogen, Cl or methyl; and Z' is F or Cl, compounds represented by the formula:

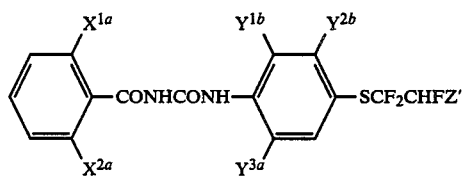

wherein $X^{1a}$, $X^{2a}$ and Z' are as defined hereinbefore; $Y^{1b}$ is hydrogen or F; $Y^{2b}$ is Br, Cl, F or methyl; and $Y^{3a}$ is hydrogen, Cl, F or methyl, and compounds represented by the formula:

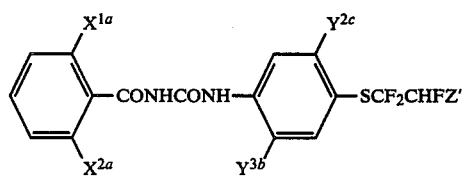

wherein $X^{1a}$, $X^{2a}$ and Z' are as defined hereinbefore; $Y^{2c}$ is Br, Cl or F; and $Y^{3b}$ is F or Cl. Particularly preferable examples of the derivatives [I] are, for example, compounds represented by the formula:

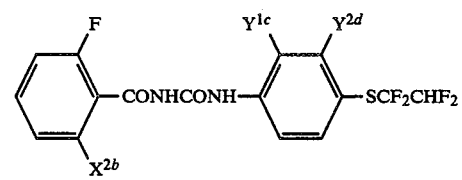

wherein $X^{2b}$ is F or Cl; $Y^{1c}$ is F or Cl; and $Y^{2d}$ is hydrogen or Cl, compounds represented by the formula:

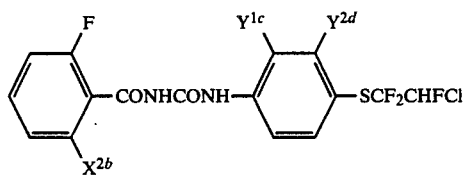

wherein the symbols are as defined hereinbefore, compounds represented by the formula:

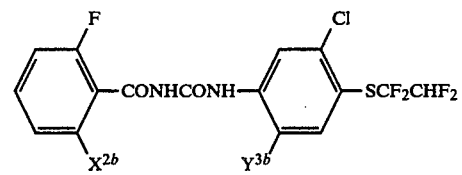

wherein $X^{2b}$ and $Y^{3b}$ are as defined hereinbefore, and compounds represented by the formula:

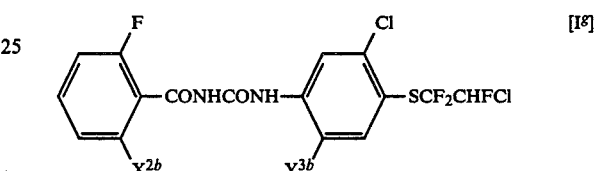

wherein the symbols are as defined hereinbefore.

The objective product [I] of the present invention can exist as isomers, when an asymmetric carbon is present in R, and may consist of individual isomers or a mixture thereof.

The benzoylurea derivatives [I] of the present invention possess enhanced insecticidal and ovicidal effects, and can produce adequate insecticidal and ovicidal effects in less used amount as compared with known analogous compounds. Besides offering the economical advantage that the applied amount can be reduced, the benzoylurea derivatives [I] of the present invention are exceedingly low in toxicity toward mammals and also low in fish toxicity, with less adverse effects on the environment, and are therefore effective for exterminating and preventing hatching of household insect pests, harmful insects parasitic on animals and plants, forest insect pests, etc. They demonstrate powerful insecticidal activities, particularly molt inhibitory activities against larvae, by allowing insect pests to directly contact, or to ingest, the compounds [I], for example, spraying them directly on animals and plants parasitized with insect pests. In addition, the compounds [I] of the present invention exhibit ovicidal and sterilizing activities and the like. The compounds [I] of the present invention, with their reduced phytotoxicity and lowered fish toxicity, provide combined characteristics of safety and advantage in utilizing for example as an agent for exterminating and preventing hatching of forest insect pests.

The compounds [I] of the present invention and insecticidal compositions containing them are effective for exterminating and preventing hatching of, for example, insect pests of the order Lepidoptera, such as *Spodopteralitura, Plutella xylostella, Pieris rapae crucivora, Chilo suppressalis, Plusia nigrisigna, Halicoverpa assulta, Pseudaletia separata, Mamestra brassicae, Adoxophyes*

*orana, Pleuroptya derogata, Cnaphalocrocis medinalis, Phthorimaea operculella, Hyphautria cunea* and *Lymantria dispar;* insect pests of the order Coleoptera, such as *Henosepilachna vigintioctopunctata, Aulacophora femoralis, Phyllotreata striolata, Oulema oryzae, Echinocnemus squameus, Leptinotorsa decemlineata, Lissorhoptrus oryzophilus* and *Anthonomus grandis;* insect pests of the order Diptera, such as *Musca domestica, Culex pipiens pallens, Tabanus trigonus, Hylemya antiqua* and *Hylemya platura;* insect pests of the order Orthoptera, such as *Locusta migratoria* and *Gryllotalpa africana;* insect pests of Dictyoptera, such as *Blattella germanica* and *Periplaneta fuliginosa;* insect pests of the order Isoptera, such as *Reticulitermes speratus;* and nematodes, such as *Aphelenchoides besseyi.*

In utilizing the benzoylurea derivatives [I] of the present invention as an insecticide or/and ovicide, such derivatives may be formulated into the application forms which general agricultural chemicals can take; namely, one or more of the compounds [I], depending upon the purpose of application, are dissolved or suspended in a suitable liquid carrier, or mixed or adsorbed with an appropriate solid carrier to process them into the desired forms of preparations, such as emulsifiable concentrate (emulsion), oil or solvent preparation, wettable powder, powder, granule, tablet, spray and ointment. As the preferable forms of preparations, there are used, for example, emulsifiable concentrate, wettable powder, powder and granule. These preparations can be prepared, if desired, in accordance with per se known methods by adding, for example, emulsifying agents, suspending agents, spreaders, penetrants, wetting agents, tackifiers and stabilizers.

The proportion of the benzoylurea derivatives [I] contained in the insecticidal or/and ovicidal composition of the present invention, for example, is suitably in the range of 5 to 90 weight % in the case of emulsifiable concentrate and wettable powder, being appropriately in the region of 0.1 to 10 weight % in the case of oil or solvent preparation and powder, and is suitably in the range of 1 to 20 weight % in the case of granule, varying with the purpose of application, and these concentrations may be suitably altered according to the purpose of application. In applying the emulsifiable concentrate and wettable powder, for example, it is recommendable to dilute and extend (e.g., to 100 to 100000 times the original volume) them properly with water and the like.

Suitable examples of the liquid carrier which is used in the preparation of the insecticidal or/and ovicidal composition of the present invention include solvents, such as water, alcohols (e.g., methyl alcohol, ethyl alcohol, ethylene glycol, etc.), ketones (e.g., acetone, methyl ethyl ketone, etc.), ethers (e.g., dioxane, tetrahydrofurane, cellosolve, etc.), aliphatic hydrocarbons (e.g., gasoline, kerosene, light oil, fuel oil, machine oil, etc.), aromatic hydrocarbons (e.g., benzene, toluene, xylene, solvent naphtha, methylnaphthalene, etc.), halogenated hydrocarbons (e.g., chloroform, carbon tetrachloride, etc.), acid amides (e.g., dimethylformamide, dimethylacetamide, etc.), esters (e.g., ethyl acetate, butyl acetate, mono-, di- or triglycerol esters of lower fatty acids of 2 to 6 carbon atoms, etc.), and nitriles (e.g., acetonitrile, etc.), and these are used in one kind or as a mixture of not less than two kinds thereof. The proportion of the liquid carrier contained in the insecticidal or/and ovicidal composition of the present invention varies depending upon the form of preparations and may, for example, range from 5 to 90 weight %, preferably from 15 to 50 weight %, in the case of emulsifiable concentrate. As the solid carrier, there are used, for example, vegetable powders (e.g., soybean meal, tobacco meal, wheat flour, wood flour, etc.), mineral powders (e.g., clays, such as kaolin, bentonite and acid clay, talcs, such as stealite powder and pencil stone or pagodite powder, silicas, such as diatomaceous earth and mica powder, etc.), and furthermore alumina, powdered sulfur, activated carbon, and the like, and these are used in one kind or as a mixture of not less than two kinds thereof. The proportion of the solid carrier contained in the insecticidal or/and ovicidal composition of the present invention varies depending upon the form of preparations, and may, for example, range from 10 to 98 weight %, preferably from 15 to 50 weight %, in the case of wettable powder, powder and granule.

As the ointment base to be used in formulating the insecticidal or/and ovicidal composition of the present invention into an ointment, there can be suitably selected, for example, polyethylene glycol [H(OCH$_2$CH$_2$)$_n$OH wherein n is about 4 to 14], pectin, polyhydric alcohol esters of higher fatty acids (having 10 to 20 carbon atoms), such as mono-, di- or triglycerol esters of stearic acid, cellulose derivatives, such as methylcellulose, sodium arginate, bentonite, higher alcohols, polyhydric alcohols, such as glycerol, petrolatum, white petrolatum, liquid paraffin, lard, all kinds of vegetable oils, lanolin, dehydrated lanolin, hardened oil and resins, in one kind, as a mixture of not less than two kinds thereof or as an admixture thereof with a variety of surface active agents. The proportion of the ointment bases contained in the insecticidal or/and ovicidal composition of the present invention may range from 50 to 95 weight %, preferably from 70 to 90 weight %.

As the surface active agent which is used, for example, as an emulsifier, spreader, penetrant or dispersing agent, in the preparation of the insecticidal or/and ovicidal composition of the present invention, there are employed, if desired, soaps, polyoxyalkylaryl esters (e.g., Nonal ®, produced by Takemoto Oils & Fats Co. of Japan, etc.), alkyl sulfates (e.g., Emaru 10 ® and Emaru 40 ®, produced by Kao-Atlas Co. of Japan, etc.), alkyl sulfonates (e.g., Neogen ® and Neogen T ®, produced by Daiichi Kogyo Seiyaku Co. of Japan: and Neopelex ®, produced by Kao-Atlas Co. of Japan, etc.), polyethylene glycol ethers (e.g., Nonipol 85 ®, Nonipol 100 ® and Nonipol 160 ®, produced by Sanyo Chemical Industries of Japan, etc.), polyhydric alcohol esters (e.g., Tween 20 ® and Tween 80 ®, produced by Kao-Atlas Co. of Japan, etc.) and the like. The proportion of these surface active agents contained in the insecticidal or/and ovicidal composition of the present invention varies depending upon the form of preparations, and may, for example, range from 1 to 20 weight %, preferably from 3 to 10 weight %, in the case of emulsifiable concentrate; from 3 to 30 weight %, preferably from 5 to 20 weight %, in the case of wettable powder; and from 0.01 to 10 weight %, preferably from 0.1 to 5 weight %, in the case of powder and granule.

Also, it is possible to apply mixtures formed by formulating the compound [I] of the present invention suitably with, for example, other kinds of insecticides (e.g., pyrethrin insecticides, organic phosphate insecticides, carbamate insecticides, natural insecticides, etc.), acaricides, nematicides, herbicides, plant hormones, plant growth regulators, fungicides and bactericides (e.g., fungicides and bactericides based on copper, chlorinated hydrocarbons, organic sulfur compounds and phenol compounds, etc.), synergists, attractants, repellents, colorants and fertilizers to such an extent as may not adversely affect the insecticidal or/and ovicidal effect produced by the benzoylurea derivatives [I] of the present invention.

The insecticidal or/and ovicidal composition of the present invention can be used in the same manner as ordinary insecticidal or/and ovicidal compositions, for example, by treatment of seedling culture boxes, spraying the stems and leaves of crops, spraying living insect bodies, underwater application in paddy fields and soil treatment. In such cases, the application amount can be varied over a wide range according to the time of application, location of application, method of application, etc., but it is generally desirable to conduct application in such a way that the active ingredient may range from 10 g to 2000 g, preferably from 50 g to 1000 g, per hectare.

Concretely, application is carried out by diluting an emulsifiable concentrate of the present invention formed by the mixing of 15 to 25 weight % of N-(2,6-difluorobenzoyl)-N'-[2-fluoro-4-(1,1,2,2-tetrafluoroethylthio)phenyl]urea or the object product [I] of the present application, 70 to 80 weight % of dimethylformamide as a liquid carrier and 3 to 10 weight % of polyoxyethylene glycol ether as a surface active agent with water containing 0.01 to 0.05% of Dain ® (produced by Takeda Chemical Industries, Ltd. of Japan) or a spreader to a concentration of 2 to 20 ppm and spraying the resulting aqueous solution on a place infested with *Spodoptera litura* at a rate of 0.5 to 5 g as an active ingredient per *are*.

The compound [I] of the present invention can be produced by reacting the compound [IV] with the compound [V]. In this reaction, the compound [IV] may be used in the proportion in the range of 1 to 1.2 moles per mole of the compound [V]. Generally, the reaction is desirably carried out in a suitable solvent, and may be conducted in inert solvent, for example, aliphatic and aromatic hydrocarbons, such as pentane, hexane, heptane, cyclohexane, petroleum ether, petroleum benzine, benzene, toluene and xylene; halogenated hydrocarbons, such as dichloromethane, chloroform, carbon tetrachloride and dichlorobenzene; ethers, such as ethyl ether, dioxane and tetrahydrofurane; nitriles, such as acetonitrile; and esters, such as ethyl acetate. The reaction temperature may generally range from about 0° to about 120° C., preferably from about 10° to 50° C. As to the reaction time, the reaction proceeds over a period of time in the range of 5 minutes to 24 hours, but may normally be terminated within a length of time in the range of 20 minutes to 2 hours. The termination of the reaction can be confirmed by thin-layer chromatography and the like.

Furthermore, the compound [I] of the present invention can be produced by reacting the compound [VI] with the compound [VII]. The compound [VII] may be used in the proportion in the range of 1 to 1.2 moles per mole of the compound [VI]. Generally, the reaction is desirably carried out in a suitable solvent, and may be conducted in inert solvent, for example, aliphatic and aromatic hydrocarbons, such as pentane, hexane, heptane, cyclohexane, petroleum ether, petroleum benzine, benzene, toluene and xylene; halogenated hydrocarbons, such as dichloromethane, chloroform, carbon tetrachloride and dichlorobenzene; ethers, such as ethyl ether, dioxane and tetrahydrofurane; nitriles, such as acetonitrile; and esters, such as ethyl acetate. The reaction temperature may from about 30° to 150° C., preferably from about 50° to 150° C. As to the reaction time, the reaction proceeds over a period of time in the range of about 30 minutes to 48 hours, but may normally be terminated within a length of time in the range of 1 to 24 hours. The termination of the reaction can be confirmed by thin-layer chromatography and the like.

Moreover, the compound [I] of the present invention can be produced, for example, by the method as shown in the following formulae.

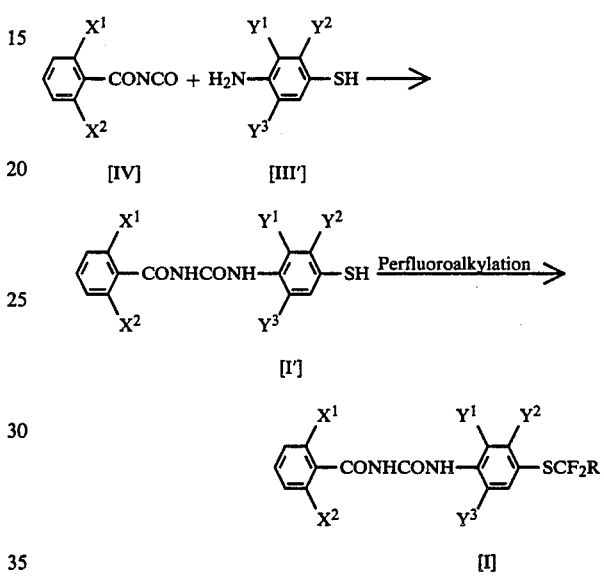

wherein the symbols are as defined hereinbefore.

The reaction of [IV] and [III'] can be carried out in a manner similar to the reaction of [IV] and [V]. The compound [IV] may be preferably used in the proportion in the range of 1 to 1.2 moles per mole of the compound [III']. The reaction normally is desirably carried out in a suitable solvent. As the solvent, there may be used those as mentioned for the reaction of [IV] and [V]. Normally, the reaction temperature may range from about 0° to about 120° C., preferably from about 10° to 50° C. As to the reaction time, the reaction proceeds over a period of time in the range of 5 minutes to 24 hours, but may normally be terminated within a length of time in the range of 20 minutes to 2 hours. The resulting compound [I'] can be isolated and purified by known means as mentioned hereinafter, but can also be subjected, as a reaction mixture without being separated, to the subsequent reaction as a starting material. The compound [I] can also be produced, in accordance with the known methods as described for example in J. Org. Chem., 29, 895–898 (1964); and J, Gen, Chem. USSR, 39, 2011–2016 (1969), by perfluoroalkylation of the compound [I'].

The compound [I] of the present invention thus obtained can be isolated and purified from the reaction mixture by per se known means, such as crystallization, recrystallization, precipitation, extraction, concentration and chromatography.

The starting compound [IV], which is used in the production of the benzoylurea derivatives [I] of the present invention, can be produced, for example, by the methods, or methods analogous thereto, as described in J. Org. Chem., 27, 3742 (1962); ibid., 30, 4306 (1965). The starting compound [V] can be produced, for example, by a method analogous to the known methods as described in J. Am. Chem. Soc., 82, 5116 (1960); J. Org. Chem., 29, 895 (1964), and besides, can also be produced, for example, by the method as shown in the following reaction formulae or methods analogous thereto.

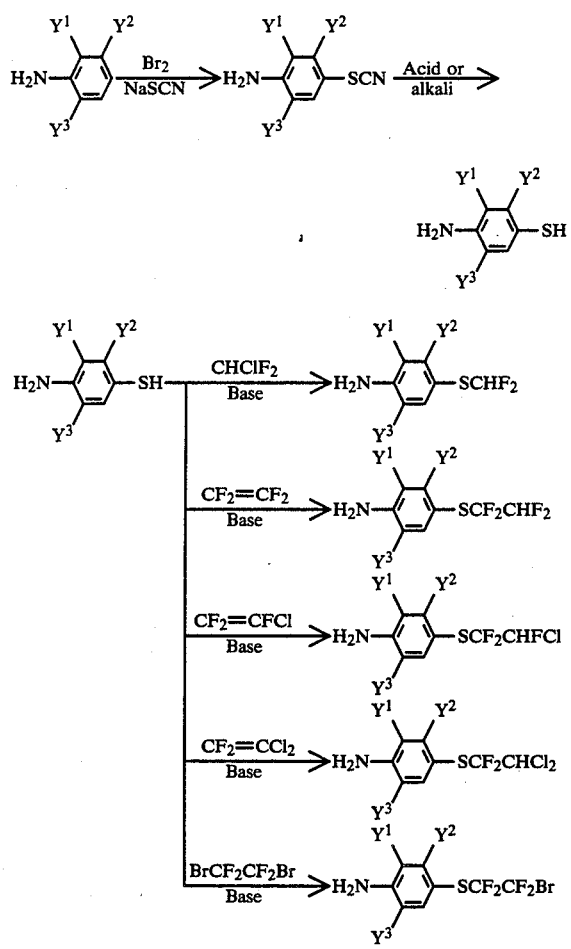

wherein $Y^1$, $Y^2$ and $Y^3$ are as defined hereinbefore. Also, the starting compound [VI] can be produced, for example, by the methods, or methods analogous thereto, as described in J. Med. Chem., 11, 814 (1963); Beilstein 'Handbuch der Organischen Chemie', 9, 336. The starting compound [VII] can be produced, for example, by the method as described in U.S. Pat. No. 4277499, the procedure of reacting the compound [V] with phosgene in accordance with the known methods, or methods analogous thereto.

The reference examples, examples and test examples are given in the following to describe the present invention more specifically, but it is to be understood that this invention shall not be limited by them. The symbols used in Reference Examples, Examples and Test Examples have the following meanings.

| | |
|---|---|
| ml: | milliliter |
| l: | liter |
| g: | gram |
| kg: | kilogram |
| Me: | methyl |

-continued

| | |
|---|---|
| %: | (weight) percent |
| b.p.: | boiling point |
| m.p.: | melting point |
| Comp'd: | Compound |
| cm: | centimeter |
| mm: | millimeter |

REFERENCE EXAMPLE 1

To 550 ml of methanol were added 111 g of 2-fluoroaniline and 240 g of sodium thiocyanate, and the mixture was cooled to 0° C. A cooled (0° C.) solution of 176 g of bromine in 500 ml of methanol saturated with sodium bromide was added dropwise to the mixture over the period of 1 hour 15 minutes under stirring. In the course of this, cooling was effected so that the internal temperature might be maintained at not more than 3° C. After the addition of bromine was completed, the reaction mixture was poured in 2 l of cold water, and 100 g of sodium hydrogencarbonate was added to make the mixture weakly alkaline. The crystals, which separated out, were recovered by filtration and washed with cold water to give 144.5 g of crude 2-fluoro-4-thiocyanatoaniline.

REFERENCE EXAMPLE 2

To a mixed solution consisting of 200 ml of conc. hydrochloric acid and 50 ml of ethanol was added 50 g of crude 2-fluoro-4-thiocyanatoaniline, and the mixture was heated under reflux for 8 hours. The crystals, which separated out upon standing overnight, were recovered by filtration and dried in a desiccator to give 44 g of crude 2-fluoro-4-mercaptoaniline hydrochloride. 44 g of crude 2-fluoro-4-mercaptoaniline hydrochloride was suspended in 100 ml of dioxane, and 30 g of triethylamine was added to the suspension. Tetrafluoroethylene was passed into the mixture over the period of 1.5 hours under heating at 50° to 60° C. with stirring (tetrafluoroethylene was generated in accordance with the conventional method by reacting 40 ml of 1,2-dibromotetrafluoroethane with 100 g of powdered zinc in methanol). After the conclusion of the reaction, the reaction mixture was diluted with water and extracted twice with 100 ml of dichloromethane. The dichloromethane extract was dehydrated with anhydrous magnesium sulfate and concentrated to dryness under reduced pressure to give 42.1 g of a yellow oily material. The oily material was distilled under reduced pressure to give 29.5 g of 2-fluoro-4-(1,1,2,2-tetrafluoroethylthio)-aniline as a colorless liquid having a boiling point of 70° to 72° C./0.6 mmHg.

By the procedures similar to the above Reference Examples, the 4-(1,1,2,2-tetrafluoroethylthio)-aniline derivatives as shown in the below table were synthesized. The results are tabulated in Table 1.

TABLE 1

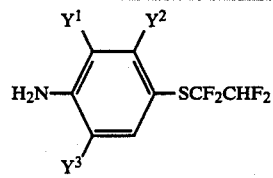

| $Y^1$ | $Y^2$ | $Y^3$ | Boiling point (melting point), °C. |
|---|---|---|---|
| Cl | H | H | 84~86/0.2 mmHg |

TABLE 1-continued

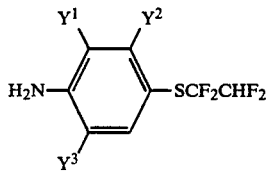

| Y¹ | Y² | Y³ | Boiling point (melting point), °C. |
|---|---|---|---|
| Me | H | H | 90–91/0.3 mmHg |
| H | F | H | 81–82/0.1~0.2 mmHg |
| H | Cl | H | 113–115/0.3 mmHg |
| H | Me | H | 97–100/0.2 mmHg |
| H | Cl | Cl | (56–56.5) |
| Cl | Cl | H | 122–125/0.3 mmHg |
| H | Cl | F | 92–93/0.15 mmHg |
| F | H | F | 63–64/0.3 mmHg |
| Br | H | H | 105–106/0.5 mmHg |
| Me | Me | H | 122/1.5 mmHg |
| H | Me | Me | 125/1.5 mmHg |
| H | Cl | Me | 115–121/1~2 mmHg |

REFERENCE EXAMPLE 3

In 20 ml of dimethylformamide was dissolved 12.0 g of 2-fluoro-4-mercaptoaniline, and 8.5 g of triethylamine was added to the solution. Trifluorochloroethylene was passed into the mixture over the period of 25 minutes under heating at 50° to 60° C. with stirring (trifluorochloroethylene was generated in accordance with the conventional method by reacting 31 g of 1,1,2-trifluorotrichloroethane with 90 g of powdered zinc in ethanol). After the conclusion of the reaction, the reaction mixture was diluted with water and extracted with toluene. The toluene layer was washed with water, 10% NaOH aqueous solution and water successively in the mentioned order, dehydrated with anhydrous magnesium sulfate and concentrated to dryness under reduced pressure to give 17.5 g of a brownish oily material. The oily material was distilled under reduced pressure to 13.7 g of 2-fluoro-4-(1,1,2-trifluoro-2-chloroethylthio)aniline as a colorless liquid having a boiling point of 95° to 98° C./0.2 mmHg.

By the similar procedure, the 4-(1,1,2-trifluoro-2-chloroethylthio)aniline derivatives as shown in the below table were synthesized. The results are tabulated in Table 2.

TABLE 2

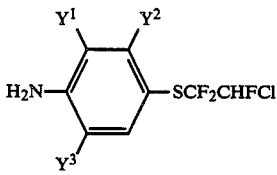

| Y¹ | Y² | Y³ | Boiling point, °C. |
|---|---|---|---|
| Cl | H | H | 108–109/0.3 mmHg |
| H | Cl | Cl | 124–126/0.15 mmHg |
| Cl | Cl | H | 128–130/0.2–0.3 mmHg |
| Me | H | H | 117–118/0.6 mmHg |
| F | H | F | 75–77/0.2 mmHg |
| Br | H | H | 133–135/1.0 mmHg |
| Me | Me | H | 140/1.5 mmHg |
| H | Me | Me | 125/0.6 mmHg |
| H | Cl | Me | Oily material (Acetyl derivative melting at 133–134° C.) |

REFERENCE EXAMPLE 4

In 20 ml of methanol was dissolved 18.4 g of 2-fluoro-4-mercaptoaniline hydrochloride, and after cooling at 0° C., 39.4 g of 28% sodium methylate was added dropwise to the solution. 30 minutes later, the insoluble matter was filtered out, and the filtrate was concentrated to dryness under reduced pressure. 200 ml of dioxane was added to the residue, and 23 g of chlorodifluoromethane was blown into the mixture under heating at 50° C. with stirring. After cooling, the reaction mixture was extracted with toluene. The toluene extract was washed with water, dehydrated with anhydrous magnesium sulfate and concentrated to dryness under reduced pressure, followed by distillation to give 11.5 g of 2-fluoro-4-difluoromethylthioaniline, b.p. of 65°–67° C./0.2 mmHg.

By the similar procedure, the 4-difluoromethylthioaniline derivatives as shown in the below table were synthesized. The results are tabulated in Table 3.

TABLE 3

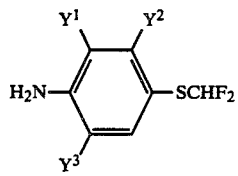

| Y¹ | Y² | Y³ | Boiling point (melting point), °C. |
|---|---|---|---|
| Cl | H | H | 96–97/0.2 mmHg |
| Me | H | H | 92–93/0.2 mmHg |
| H | F | H | 103–104/1 mmHg |
| H | Cl | H | 114–115/0.2 mmHg |
| Cl | Cl | H | (57–58) |
| F | H | F | 80–82/0.3 mmHg |
| Br | H | H | 118–119/0.2–0.3 mmHg |

EXAMPLE 1

In 15 ml of toluene was dissolved 2.6 g of 2-fluoro-4-(1,1,2-trifluoro-2-chloroethylthio)aniline, and 1.8 g of 2,6-difluorobenzoylisocyanate was added dropwise to the solution at room temperature (20° to 25° C.). After the reaction was allowed to proceed at the same temperature for 1 hour, the crystals, which separated out, were recovered by filtration and washed wiht toluene to give 3.6 g of N-(2,6-difluorobenzoyl)-N'-[2-fluoro-4-(1,1,2-trifluoro-2-chloroethylthio)phenyl]urea (Compound No. 39), m.p. of 172°–173° C.

Elemental analysis, for $C_{16}H_9N_2F_6ClO_2S$. Calcd.: C, 43.40%; H, 2.05%; N, 6.33%. Found: C, 43.50%; H, 2.05%; N, 6.29%.

EXAMPLE 2

In 20 ml of toluene was dissolved 1.0 g of 2-fluoro-4-(1,1,2,2-tetrafluoroethylthio)aniline, and 0.8 g of 2,6-difluorobenzoyl isocyanate was added dropwise to the solution at room temperature (20° to 25° C.). After the reaction was allowed to proceed at the same temperature for 30 minutes, the crystals, which separated out, were recovered by filtration and washed with toluene to give 1.5 g of N-(2,6-difluorobenzoyl)-N'-[2-fluoro-4-(1,1,2,2-tetrafluoro-ethylthio)phenyl]urea (Compound No. 1), m.p. of 177°–179° C.

Elemental analysis, for $C_{16}H_9N_2F_7O_2S$. Calcd.: C, 45.08%; H, 2.13%; N, 6.57%. Found: C, 45.06%; H, 2.07%; N, 6.59%.

EXAMPLE 3

In 15 ml of toluene was dissolved 1.0 g of 2-fluoro-4-difluoromethylthioaniline, and 1.0 g of 2,6-difluorobenzoyl isocyanate was added dropwise to the solution at room temperature (20° to 25° C.). After the reaction was allowed to proceed at the same temperature for 30 minutes, the crystals, which separated out, were recovered by filtration and washed with toluene to give 1.5 g of N-(2,6-difluorobenzoyl)-N'-(2-fluoro-4-difluoromethylthiophenyl)urea (Compound No. 55). Recrystallization from acetone gave crystals having a melting point of 172°-173° C.

Elemental analysis, for $C_{15}H_9N_2F_5O_2S$. Calcd.: C, 47.88%; H, 2.41%; N, 7.44%. Found: C, 47.94%; H, 2.34%; N, 7.37%.

EXAMPLE 4

To 140 ml of 4% phosgen-toluene solution was added 3.6 g of 2-fluoro-4-(1,1,2,2-tetrafluoroethylthio)aniline, and the mixture was heated under reflux for 3 hours. After the conclusion of the reaction, the reaction mixture was concentrated to dryness under reduced pressure to give 2-fluoro-4-(1,1,2,2-tetrafluoroethylthio)phenyl isocyanate as an oily material. The oily material was dissolved in 50 ml of xylene, and 1.5 g of 2,6-difluorobenzamide was added to the solution, followed by heating under reflux for 20 hours. After the conclusion of the reaction, the reaction mixture was cooled (0° C.), and the crystals which separated out were recovered by filtration, and further recrystallized from acetone to give N-(2,6-difluorobenzoyl)-N'-[2-fluoro-4-(1,1,2,2-tetrafluoroethylthio)phenyl]urea (Compound No. 1) as crystals having a m.p. of 177°-179° C. The resulting compound was found to show no decrease in melting point even when admixed with the authentic sample as obtained in Example 2.

By the procedures similar to the above examples, the benzoylurea derivatives [I] as shown in the below table were synthesized. The results are tabulated in Table 4, in which the compounds as synthesized in Examples 1 through 3 are included.

TABLE 4

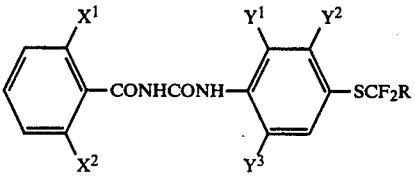

| Comp'd No. | $X^1$ | $X^2$ | $Y^1$ | $Y^2$ | $Y^3$ | R | Melting point, °C. |
|---|---|---|---|---|---|---|---|
| 1 | F | F | F | H | H | $CHF_2$ | 177–179 |
| 2 | F | Cl | F | H | H | $CHF_2$ | 195–196.5 |
| 3 | Cl | Cl | F | H | H | $CHF_2$ | 228–230 |
| 4 | Cl | H | F | H | H | $CHF_2$ | 152–153.5 |
| 5 | F | F | Cl | H | H | $CHF_2$ | 145 |
| 6 | F | Cl | Cl | H | H | $CHF_2$ | 169–171 |
| 7 | Cl | Cl | Cl | H | H | $CHF_2$ | 200–201 |
| 8 | Cl | H | Cl | H | H | $CHF_2$ | 130–131 |
| 9 | F | F | Me | H | H | $CHF_2$ | 141–142 |
| 10 | F | Cl | Me | H | H | $CHF_2$ | 147–149 |
| 11 | Cl | Cl | Me | H | H | $CHF_2$ | 175–177 |
| 12 | Cl | H | Me | H | H | $CHF_2$ | 125–126 |
| 13 | F | F | H | F | H | $CHF_2$ | 190–192 |
| 14 | F | Cl | H | F | H | $CHF_2$ | 191–192 |

TABLE 4-continued

| Comp'd No. | $X^1$ | $X^2$ | $Y^1$ | $Y^2$ | $Y^3$ | R | Melting point, °C. |
|---|---|---|---|---|---|---|---|
| 15 | Cl | Cl | H | F | H | $CHF_2$ | 209–211 |
| 16 | Cl | H | H | F | H | $CHF_2$ | 189–190 |
| 17 | F | F | H | Cl | H | $CHF_2$ | 186–187 |
| 18 | F | Cl | H | Cl | H | $CHF_2$ | 191–193 |
| 19 | Cl | Cl | H | Cl | H | $CHF_2$ | 187–188 |
| 20 | Cl | H | H | Cl | H | $CHF_2$ | 202–203 |
| 21 | F | F | H | Me | H | $CHF_2$ | 191–192 |
| 22 | F | Cl | H | Me | H | $CHF_2$ | 171–172 |
| 23 | Cl | Cl | H | Me | H | $CHF_2$ | 194–196 |
| 24 | Cl | H | H | Me | H | $CHF_2$ | 176–177 |
| 25 | F | F | H | Cl | Cl | $CHF_2$ | 189–190 |
| 26 | F | Cl | H | Cl | Cl | $CHF_2$ | 206.5–207.5 |
| 27 | Cl | Cl | H | Cl | Cl | $CHF_2$ | 190–191 |
| 28 | Cl | H | H | Cl | Cl | $CHF_2$ | 182 |
| 29 | F | F | Cl | Cl | H | $CHF_2$ | 153–153.5(2/5 $CHCl_3$)* |
| 30 | F | Cl | Cl | Cl | H | $CHF_2$ | 187–189(1/10 $CHCl_3$)* |
| 31 | Cl | Cl | Cl | Cl | H | $CHF_2$ | 202–204 |
| 32 | Cl | H | Cl | Cl | H | $CHF_2$ | 187–189 |
| 33 | F | F | H | Cl | F | $CHF_2$ | 179–180 |
| 34 | Cl | H | H | Cl | F | $CHF_2$ | 194–195 |
| 35 | F | F | F | H | F | $CHF_2$ | 197–198 |
| 36 | F | Cl | F | H | F | $CHF_2$ | 191–192 |
| 37 | Cl | Cl | F | H | F | $CHF_2$ | 190–192 |
| 38 | Cl | H | F | H | F | $CHF_2$ | 162 |
| 39 | F | F | F | H | H | CHFCl | 172–173 |
| 40 | F | Cl | F | H | H | CHFCl | 190–191(1/14 toluene)* |
| 41 | Cl | Cl | F | H | H | CHFCl | 207–208 |
| 42 | Cl | H | F | H | H | CHFCl | 150–151 |
| 43 | F | F | H | F | H | CHFCl | 189–190 |
| 44 | F | F | H | Cl | Cl | CHFCl | 181–183(1/10 $CHCl_3$)* |
| 45 | F | Cl | H | Cl | Cl | CHFCl | 200–203(1/10 $CHCl_3$)* |
| 46 | Cl | Cl | H | Cl | Cl | CHFCl | 191–193 |
| 47 | Cl | H | H | Cl | Cl | CHFCl | 162–163(1/5 $CHCl_3$)* |
| 48 | F | F | Cl | Cl | H | CHFCl | 158–159 |
| 49 | F | Cl | Cl | Cl | H | CHFCl | 177–178 |
| 50 | Cl | Cl | Cl | Cl | H | CHFCl | 176–178(0.04 toluene)* |
| 51 | Cl | H | Cl | Cl | H | CHFCl | 179–180 |
| 52 | F | F | F | H | F | CHFCl | 196 |
| 53 | Cl | Cl | F | H | F | CHFCl | 197 |
| 54 | Cl | H | F | H | F | CHFCl | 159 |
| 55 | F | F | F | H | H | H | 172–173 |
| 56 | F | Cl | F | H | H | H | 196–197 |
| 57 | Cl | Cl | F | H | H | H | 212–213 |
| 58 | Cl | H | F | H | H | H | 150–152 |
| 59 | F | F | Cl | H | H | H | 187–188 |
| 60 | F | Cl | Cl | H | H | H | 188–189 |
| 61 | Cl | Cl | Cl | H | H | H | 221–222 |
| 62 | Cl | H | Cl | H | H | H | 145–146 |
| 63 | F | F | Me | H | H | H | 200–201 |
| 64 | F | Cl | Me | H | H | H | 156–157 |
| 65 | Cl | Cl | Me | H | H | H | 180–182 |
| 66 | Cl | H | Me | H | H | H | 155–156 |
| 67 | F | F | H | F | H | H | 183.5–184.5 |
| 68 | F | Cl | H | F | H | H | 191–192.5 |
| 69 | Cl | Cl | H | F | H | H | 202–204 |
| 70 | Cl | H | H | F | H | H | 196–197 |
| 71 | F | F | H | Cl | H | H | 171–172 |
| 72 | F | Cl | H | Cl | H | H | 217–218 |
| 73 | Cl | Cl | H | Cl | H | H | 219–220 |
| 74 | Cl | H | H | Cl | H | H | 200–201 |
| 75 | F | F | H | Br | H | H | 179–180.5 |
| 76 | F | Cl | H | Br | H | H | 201–202 |
| 77 | Cl | Cl | H | Br | H | H | 208–209 |
| 78 | Cl | H | H | Br | H | H | 200–201 |

TABLE 4-continued

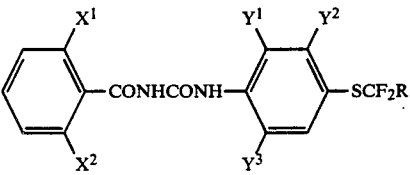

$$[I]$$

| Comp'd No. | $X^1$ | $X^2$ | $Y^1$ | $Y^2$ | $Y^3$ | R | Melting point, °C. |
|---|---|---|---|---|---|---|---|
| 79 | F | F | H | Me | H | H | 185–186 |
| 80 | F | Cl | H | Me | H | H | 213–214 |
| 81 | Cl | Cl | H | Me | H | H | 222–223 |
| 82 | Cl | H | H | Me | H | H | 181–182 |
| 83 | F | F | H | Cl | Cl | H | 183–184 |
| 84 | F | Cl | H | Cl | Cl | H | 215–217 |
| 85 | Cl | Cl | H | Cl | Cl | H | 215–217 |
| 86 | Cl | H | H | Cl | Cl | H | 168–169 |
| 87 | F | F | Cl | Cl | H | H | 223–224 |
| 88 | F | Cl | Cl | Cl | H | H | 228–230 |
| 89 | Cl | Cl | Cl | Cl | H | H | 233–235 |
| 90 | Cl | H | Cl | Cl | H | H | 206–207 |
| 91 | F | F | H | Cl | F | H | 176–177 |
| 92 | F | Cl | H | Cl | F | H | 214–216 |
| 93 | Cl | Cl | H | Cl | F | H | 217–219 |
| 94 | Cl | H | H | Cl | F | H | 169–170 |
| 95 | F | F | F | H | F | H | 185 |
| 96 | Cl | Cl | F | H | F | H | 212 |
| 97 | Cl | H | F | H | F | H | 174 |
| 98 | F | F | Me | H | Me | H | 205–206 |
| 99 | Cl | H | Me | H | Me | H | 176–178 |
| 100 | F | F | Br | H | H | $CHF_2$ | 138–139 |
| 101 | Cl | H | Br | H | H | $CHF_2$ | 130–131 |
| 102 | F | F | H | Me | Me | $CHF_2$ | 151–152 |
| 103 | Cl | H | H | Me | Me | $CHF_2$ | 157–158 |
| 104 | F | F | Me | Me | H | $CHF_2$ | 145–146 |
| 105 | Cl | H | Me | Me | H | $CHF_2$ | 145–146 |
| 106 | F | F | H | Cl | Me | $CHF_2$ | 158–159 |
| 107 | Cl | H | H | Cl | Me | $CHF_2$ | 160–161 |
| 108 | F | F | Br | H | H | CHFCl | 148–149 |
| 109 | Cl | H | Br | H | H | CHFCl | 131–132 |
| 110 | F | F | H | Me | Me | CHFCl | 146–147 |
| 111 | Cl | H | H | Me | Me | CHFCl | 148–149 |
| 112 | F | F | Me | Me | H | CHFCl | 150–151 |
| 113 | Cl | H | Me | Me | H | CHFCl | 145–146 |
| 114 | F | F | H | Cl | Me | CHFCl | 157–159 |
| 115 | Cl | H | H | Cl | Me | CHFCl | 173–174 |
| 116 | F | F | Cl | H | H | CHFCl | 133–134 |
| 117 | F | Cl | Cl | H | H | CHFCl | 176–177 |
| 118 | Cl | Cl | Cl | H | H | CHFCl | 180–181 |
| 119 | Cl | H | Cl | H | H | CHFCl | 136–137 |

*The parenthesized figures following the melting points indicate the content of impurities contained. Me denotes a methyl group.

EXAMPLE 5

(Emulsifiable concentrate)

| Compound No. 1 | 20 weight % |
|---|---|
| Dimethylformamide | 75 weight % |
| Polyoxyethylene glycol ether (Nonipol 85 ®, produced by Sanyo Chemical Ind. of Japan) | 5 weight % |

An emulsifiable concentrate formed by mixing the above ingredients (to be sprayed after diluting with water to a desired concentration on the occasion of use).

EXAMPLE 6

(Wettable powder)

| Compound No. 39 | 25 weight % |
|---|---|
| Polyoxyethylene glycol ether (Nonipol 85 ®, produced by Sanyo Chemical Ind. of Japan) | 6 weight % |
| Diatomaceous earth | 69 weight % |

A wettable powder formed by mixing the above ingredients (to be sprayed after diluting with water to a desired concentration on the occasion of use).

EXAMPLE 7

(Wettable powder)

| Compound No. 55 | 25 weight % |
|---|---|
| Sodium lignin sulfonate | 5 weight % |
| Polyoxyethylene glycol ether (Nonipol 85 ®, produced by Sanyo Chemical Ind. of Japan) | 5 weight % |
| Clay | 65 weight % |

A wettable powder formed by uniformly mixing and pulverizing the above ingredients (to be sprayed after diluting with water to a desired concentration on the occasion of use).

EXAMPLE 8

(Powder)

| Compound No. 1 | 10 weight % |
|---|---|
| Clay | 89.3 weight % |
| Silicone | 0.5 weight % |
| Polyethylene glycol ether | 0.2 weight % |

A powder formed by uniformly mixing and pulverizing the above ingredients.

EXAMPLE 9

(Granule)

| Compound NO. 1 | 5 weight % |
|---|---|
| Clay | 72 weight % |
| Bentonite | 20 weight % |
| Polyoxyethylene glycol ether (Nonipol 85 ®, produced by Sanyo Chemical Ind. of Japan) | 0.5 weight % |
| Sodium carboxymethyl cellulose | 2.5 weight % |

The above ingredients were uniformly mixed and pulverized, and water of 8 weight % against the total weight was added to the mixture, followed by kneading thoroughly. Subsequently, the mixture was processed into granules, which were dried to a granular preparation, in accordance with the conventional method.

EXAMPLE 10

(Granule)

| Compound No. 39 | 2 weight % |
|---|---|
| Sodium lignin sulfonate | 5 weight % |
| Bentonite | 93 weight % |

The above ingredients were uniformly mixed and pulverized, and water of 10 weight % against the total weight was added to the mixture, followed by kneading thoroughly. Subsequently, the mixture was processed into granules, which were dried to a granular preparation, in accordance with the conventional method.

TEST EXAMPLE 1

Insecticidal effect against *Spodoptera litura*

A test compound was processed into an emulsifiable concentrate in accordance with the same formulation as described in Example 5, followed by dilution with water to prepare 2 and 10 ppm treatment solutions (admixed with 0.03% of Spreader Dain ®). 20 ml each of the treatment solutions were sprayed to soybean seedlings (14 days after germination) grown in a pot in a spray chamber with use of a spray gun (with a spraying pressure of 1 kg/cm$^2$). One day after spraying, two treated leaves were cut off and placed in an ice-cream cup (with a diameter of 6 cm and a depth of 4 cm), in which 10 third-instar larvae of *Spodoptera litura* were released. After releasing, the above cup was placed in a room (25° C.), and examined for a number of dead larvae 4 days later. The test was repeated twice, whereby the test results were expressed in terms of rate of death (%) as shown in Table 5.

TEST EXAMPLE 2

Insecticidal effect against *Plutella xylostella*

In accordance with the same formulation and preparation method as described in Test Example 1, there were prepared 3.3 and 10 ppm treatment solutions of a test compound, and 20 ml each of the treatment solutions were sprayed to seedlings (25 days after germination) of Hatsuka-daikon (a kind of radish) grown in a pot by the same spraying procedure as in Test Example 1. 2 hours after spraying, two treated leaves were cut off and placed in an ice-cream cup, in which 10 second-instar larvae of *Plutella xylostella* were released. After releasing, the above cup was placed in a room (25° C.) and examined for a number of dead larvae 4 days later. The test was repeated twice, whereby the test results were expressed in terms of rate of death (%) as shown in Table 6.

TEST EXAMPLE 3

Insecticidal effect against *Adoxophyes orana*

In accordance with the same formulation as described in Example 6, a test compound was processed into a wettable powder, followed by dilution with water to prepare 5 and 20 ppm treatment solutions (admixed with 0.03% of Spreader Dain ®). The whole leaves of soybean seedlings (14 days after germination) grown in a pot were immersed in each of the treatment solutions for 10 seconds and air-dried, and two leaves thus treated were cut off and placed in an ice-cream cup, in which 10 second-instar larvae of *Adoxophyes orana* were released. After releasing, the above cup was placed in a room (25° C.) and examined for a number of dead larvae 7 days later. The test was repeated twice, whereby the test results were expressed in terms of rate of death (%) as shown in Table 7.

TEST EXAMPLE 4

Insecticidal effect against *Henosepilachna vigintioctopunctata*

In accordance with the same formulation and preparation method as described in Test Example 1, there were prepared 4 and 20 ppm treatment solutions of a test compound, and a cut piece (5 mm thick) of potato was immersed in each of the treatment solutions for 10 seconds, air-dried and transferred into a Petri dish (with a diameter of 9 cm), in which 10 second-instar larvae of *Henosepilachna vigintioctopunctata* were released. After releasing, the Petri dish was placed in a room (25° C.), and examined for a number of dead larvae 7 days later. The test was repeated twice, whereby the test results were expressed in terms of rate of death (%) as shown in Table 8.

In the respective tests mentioned above, the following compounds were used as a control compound.

Control compound A=Dimilin:
N-(4-chlorophenyl)-N'-(2,6-difluorobenzoyl)urea (Diflubenzuron)

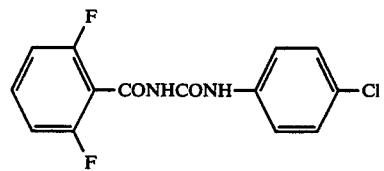

Control compound B=Acephate:
N-acetylphosphoramidothiol acid O,S-dimethyl

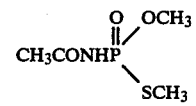

Control compound C=the compound in European Patent Publication No. 71279.

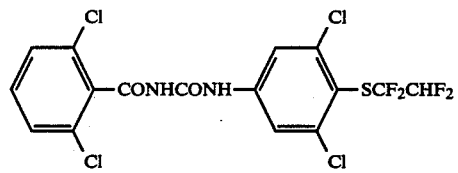

TABLE 5:

| Comp'd No. | *Spodoptera litura* rate of death (%) | | Comp'd No. | *Spodoptera litura* rate of death (%) | |
|---|---|---|---|---|---|
| | 2 ppm | 10 ppm | | 2 ppm | 10 ppm |
| 1 | 100 | 100 | 58 | 100 | 100 |
| 2 | 100 | 100 | 59 | 100 | 100 |
| 3 | 100 | 100 | 60 | 100 | 100 |
| 4 | 100 | 100 | 62 | 95 | 100 |
| 5 | 100 | 100 | 63 | 100 | 100 |
| 6 | 100 | 100 | 64 | 100 | 100 |
| 7 | — | 100 | 65 | — | 100 |
| 8 | 100 | 100 | 66 | 100 | 100 |
| 9 | 100 | 100 | 69 | — | 100 |
| 10 | 100 | 100 | 71 | — | 100 |
| 11 | 90 | 100 | 72 | — | 100 |
| 12 | 100 | 100 | 75 | 90 | 100 |
| 13 | 85 | 100 | 76 | 95 | 100 |
| 14 | 100 | 100 | 78 | 100 | 100 |
| 15 | 100 | 100 | 79 | — | 100 |
| 16 | — | 100 | 80 | 90 | 100 |
| 17 | 100 | 100 | 82 | — | 100 |
| 18 | 100 | 100 | 83 | 100 | 100 |
| 19 | 85 | 100 | 86 | 95 | 100 |
| 20 | 95 | 100 | 87 | 100 | 100 |
| 21 | 100 | 100 | 88 | 100 | 100 |
| 22 | 100 | 100 | 91 | 100 | 100 |
| 23 | 100 | 100 | 92 | — | 100 |
| 24 | 100 | 100 | 94 | 100 | 100 |
| 25 | 100 | 100 | 95 | 100 | 100 |
| 26 | 85 | 100 | 96 | — | 100 |
| 28 | 100 | 100 | 97 | 100 | 100 |
| 29 | 100 | 100 | 98 | 100 | 100 |
| 30 | 100 | 100 | 100 | 100 | 100 |

TABLE 5:-continued

| Comp'd No. | Spodoptera litura rate of death (%) 2 ppm | 10 ppm | Comp'd No. | Spodoptera litura rate of death (%) 2 ppm | 10 ppm |
|---|---|---|---|---|---|
| 31 | — | 100 | 101 | 95 | 100 |
| 32 | 100 | 100 | 102 | 100 | 100 |
| 33 | 100 | 100 | 103 | — | 100 |
| 34 | 100 | 100 | 104 | 100 | 100 |
| 35 | 100 | 100 | 105 | 100 | 100 |
| 36 | 100 | 100 | 106 | 100 | 100 |
| 37 | 85 | 100 | 107 | 95 | 100 |
| 38 | 100 | 100 | 108 | 100 | 100 |
| 39 | 100 | 100 | 109 | 100 | 100 |
| 40 | 100 | 100 | 110 | 100 | 100 |
| 41 | 100 | 100 | 111 | 100 | 100 |
| 42 | 100 | 100 | 112 | 100 | 100 |
| 43 | 100 | 100 | 113 | 100 | 100 |
| 44 | 100 | 100 | 114 | 100 | 100 |
| 45 | 100 | 100 | 115 | 100 | 100 |
| 47 | 100 | 100 | 116 | 100 | 100 |
| 48 | 100 | 100 | 117 | 100 | 100 |
| 49 | 100 | 100 | 118 | 100 | 100 |
| 50 | 100 | 100 | 119 | 95 | 100 |
| 51 | 100 | 100 | Control comp'd A | 10 | 95 |
| 52 | 100 | 100 | | | |
| 53 | 95 | 100 | Control comp'd B | 10 | 0 |
| 54 | 100 | 100 | | | |
| 55 | 100 | 100 | Control comp'd C | 30 | — |
| 56 | 100 | 100 | | | |
| 57 | — | 100 | none | 0 | 0 |

TABLE 6

| Comp'd No. | Plutella xylostella rate of death (%) 3.3 ppm | 10 ppm | Comp'd No. | Plutella xylostella rate of death (%) 3.3 ppm | 10 ppm |
|---|---|---|---|---|---|
| 1 | 100 | 100 | 68 | 100 | 100 |
| 2 | 100 | 100 | 69 | — | 100 |
| 4 | 100 | 100 | 71 | 100 | 100 |
| 5 | 100 | 100 | 75 | 90 | 100 |
| 6 | 100 | 100 | 76 | 95 | 100 |
| 8 | 100 | 100 | 78 | 100 | 100 |
| 9 | 100 | 100 | 79 | — | 100 |
| 10 | 95 | 100 | 80 | 90 | 100 |
| 12 | 95 | 100 | 82 | — | 100 |
| 13 | 100 | 100 | 83 | 100 | 100 |
| 14 | 100 | 100 | 86 | 95 | 100 |
| 15 | — | 100 | 87 | 100 | 100 |
| 16 | 95 | 100 | 88 | 100 | 100 |
| 17 | 100 | 100 | 91 | 100 | 100 |
| 18 | 100 | 100 | 92 | — | 100 |
| 21 | 100 | 100 | 94 | 100 | 100 |
| 22 | 100 | 100 | 95 | 100 | 100 |
| 24 | 100 | 100 | 96 | — | 100 |
| 25 | 100 | 100 | 97 | 100 | 100 |
| 26 | 100 | 100 | 98 | 100 | 100 |
| 28 | 100 | 100 | 100 | 100 | 100 |
| 29 | 100 | 100 | 101 | 95 | 100 |
| 30 | 100 | 100 | 102 | 100 | 100 |
| 32 | 100 | 100 | 103 | — | 100 |
| 33 | 100 | 100 | 104 | 100 | 100 |
| 34 | 100 | 100 | 105 | 100 | 100 |
| 35 | 100 | 100 | 106 | 100 | 100 |
| 38 | 100 | 100 | 107 | 95 | 100 |
| 39 | 100 | 100 | 108 | 100 | 100 |
| 40 | 100 | 100 | 109 | 100 | 100 |
| 41 | 100 | 100 | 110 | 100 | 100 |
| 42 | 100 | 100 | 111 | 100 | 100 |
| 43 | 100 | 100 | 112 | 100 | 100 |
| 44 | 100 | 100 | 113 | 100 | 100 |
| 45 | 100 | 100 | 114 | 100 | 100 |
| 47 | 100 | 100 | 115 | 100 | 100 |
| 49 | 100 | 100 | 116 | 100 | 100 |
| 51 | 100 | 100 | 117 | 100 | 100 |
| 52 | — | 100 | 118 | 100 | 100 |
| 53 | 100 | 100 | 119 | 95 | 100 |
| 54 | 100 | 100 | Control | 10 | 95 |

TABLE 6-continued

| Comp'd No. | Plutella xylostella rate of death (%) 3.3 ppm | 10 ppm | Comp'd No. | Plutella xylostella rate of death (%) 3.3 ppm | 10 ppm |
|---|---|---|---|---|---|
| 55 | 100 | 100 | comp'd A | | |
| 56 | 100 | 100 | Control | 0 | 0 |
| 58 | 100 | 100 | comp'B | | |
| 62 | — | 100 | Control | 30 | — |
| 63 | 100 | 100 | comp'd C | | |
| 64 | — | 100 | none | 0 | 0 |
| 67 | 100 | 100 | | | |

TABLE 7

| Comp'd No. | Adoxophyes orana rate of death (%) 5 ppm | 20 ppm | Comp'd No. | Adoxophyes orana rate of death (%) 5 ppm | 20 ppm |
|---|---|---|---|---|---|
| 1 | 80 | 100 | 50 | 80 | 100 |
| 2 | 100 | 100 | 51 | 100 | 100 |
| 3 | — | 100 | 52 | 95 | 100 |
| 4 | 95 | 100 | 56 | 95 | 100 |
| 5 | 100 | 100 | 87 | — | 100 |
| 6 | 90 | 100 | 100 | 100 | 100 |
| 8 | 85 | 100 | 102 | 95 | 100 |
| 9 | 100 | 100 | 103 | 95 | 100 |
| 10 | 100 | 100 | 104 | 100 | 100 |
| 11 | 80 | 100 | 105 | 100 | 100 |
| 12 | 90 | 100 | 106 | 100 | 100 |
| 14 | 95 | 100 | 107 | — | 95 |
| 22 | 95 | 100 | 108 | 100 | 100 |
| 25 | 100 | 100 | 109 | 95 | 100 |
| 26 | — | 100 | 110 | 95 | 100 |
| 28 | — | 100 | 111 | 95 | 100 |
| 29 | 100 | 100 | 112 | 100 | 100 |
| 30 | 100 | 100 | 113 | 100 | 100 |
| 32 | 90 | 100 | 114 | 95 | 100 |
| 33 | 100 | 100 | 115 | 90 | 100 |
| 34 | 100 | 100 | 116 | 100 | 100 |
| 39 | 100 | 100 | 117 | 100 | 100 |
| 40 | 100 | 100 | 118 | 95 | 100 |
| 41 | 100 | 100 | 119 | 100 | 100 |
| 42 | 95 | 100 | Control comp'd A | 0 | 0 |
| 44 | 100 | 100 | | | |
| 45 | 90 | 100 | Control comp'd B | 0 | 0 |
| 47 | 95 | 100 | | | |
| 48 | 100 | 100 | none | 0 | 0 |
| 49 | 100 | 100 | | | |

TABLE 8

| Comp'd No. | Henosepilachna vigintiocto-punctata rate of death (%) 4 ppm | 20 ppm | No. | Henosepilachna vigintiocto-punctata rate of death (%) 4 ppm | 20 ppm |
|---|---|---|---|---|---|
| 2 | 100 | 100 | 50 | 85 | 100 |
| 3 | 100 | 100 | 52 | 100 | 100 |
| 4 | 100 | 100 | 53 | 95 | 95 |
| 5 | 100 | 100 | 54 | 100 | 100 |
| 7 | 95 | 95 | 58 | — | 95 |
| 8 | — | 95 | 59 | — | 100 |
| 10 | 100 | 100 | 63 | 90 | 100 |
| 11 | 100 | 100 | 64 | 95 | 100 |
| 13 | 90 | 100 | 67 | 90 | 100 |
| 14 | 100 | 100 | 68 | 100 | 100 |
| 15 | 100 | 100 | 69 | 90 | 100 |
| 16 | — | 100 | 70 | — | 100 |
| 17 | 100 | 100 | 75 | 90 | 100 |
| 18 | 100 | 100 | 76 | 95 | 100 |
| 20 | 90 | 100 | 77 | — | 90 |
| 21 | 95 | 95 | 78 | 100 | 100 |
| 23 | 90 | 100 | 79 | 95 | 100 |
| 24 | 100 | 100 | 81 | 95 | 95 |
| 25 | 85 | 100 | 83 | 95 | 95 |

TABLE 8-continued

| Comp'd No. | Henosepilachna vigintiocto- punctata rate of death (%) | | No. | Henosepilachna vigintiocto- punctata rate of death (%) | |
|---|---|---|---|---|---|
| | 4 ppm | 20 ppm | | 4 ppm | 20 ppm |
| 26 | 100 | 100 | 84 | 95 | 95 |
| 27 | 100 | 100 | 87 | 100 | 100 |
| 28 | 100 | 100 | 88 | — | 95 |
| 29 | 100 | 100 | 91 | 100 | 100 |
| 30 | 100 | 100 | 102 | 95 | 100 |
| 31 | 95 | 100 | 103 | 90 | 95 |
| 32 | 100 | 100 | 104 | 90 | 95 |
| 35 | — | 95 | 105 | 100 | 100 |
| 36 | 80 | 95 | 107 | 90 | 100 |
| 37 | 100 | 100 | 110 | 95 | 100 |
| 38 | 75 | 90 | 111 | 95 | 100 |
| 39 | 100 | 100 | 112 | 100 | 100 |
| 40 | 95 | 95 | 113 | 90 | 100 |
| 41 | 100 | 100 | 114 | — | 100 |
| 42 | 75 | 100 | Control comp'd A | 60 | 80 |
| 43 | 100 | 100 | | | |
| 44 | 100 | 100 | Control comp'd B | 0 | 0 |
| 45 | 100 | 100 | | | |
| 46 | 100 | 100 | Control comp'C | — | 50 |
| 47 | 95 | 100 | | | |
| 48 | 90 | 100 | none | 0 | 0 |
| 49 | 95 | 100 | | | |

What we claim is:

1. A compound of the formula:

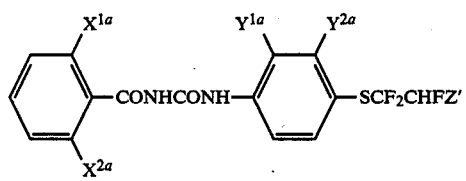

wherein $X^{1a}$ is F or Cl; $X^{2a}$ is F or Cl in the case of $X^{1a}$ being F, or hydrogen or Cl in the case of $X^{1a}$ being Cl; $Y^{1a}$ is Br, Cl, F or methyl; $Y^{2a}$ is hydrogen, Cl or methyl; and $Z'$ is F or Cl.

2. A compound selected from the group consisting of (i) a compound of the formula:

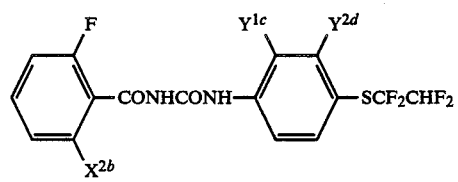

wherein $X^{2b}$ is F or Cl; $Y^{1c}$ is F or Cl; and $Y^{2d}$ is hydrogen or Cl, (ii) a compound of the formula:

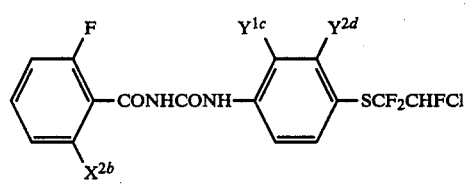

wherein the symbols are as defined hereinbefore, (iii) a compound of the formula:

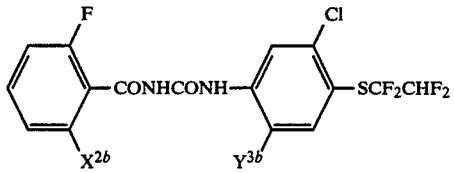

wherein $X^{2b}$ is as defined hereinbefore; and $Y^{3b}$ is F or Cl, and (iv) a compound of the formula:

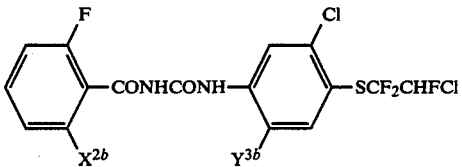

wherein the symbols are as defined hereinbefore.

3. A compound of the formula:

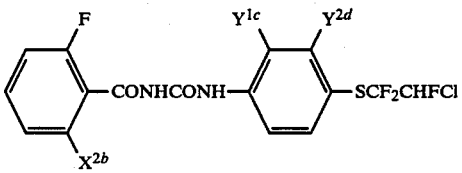

wherein $X^{2b}$ is F or Cl; $Y^{1c}$ is F or Cl; and $Y^{2d}$ is hydrogen or Cl.

4. A compound as claimed in claim 3, which is N-(2,6-difluorobenzoyl)-N'-[2-fluoro-4-(1,1,2-trifluoro-2-chloroethylthio)phenyl]urea.

5. A compound as claimed in claim 1, which is N-(2,6-difluorobenzoyl)-N'-[2-fluoro-4-(1,1,2,2-tetrafluoroethylthio)phenyl]urea.

6. A compound as claimed in claim 1, which is N-(2,6-difluorobenzoyl)-N'-[2-chloro-4-(1,1,2,2-tetrafluoroethylthio)phenyl]urea.

7. A compound of the formula:

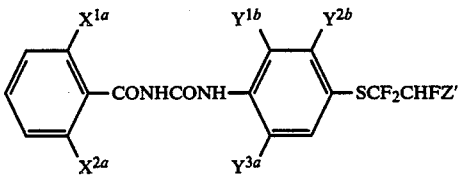

wherein $X^{1a}$ is F or Cl; $X^{2a}$ is F or Cl in the case of $X^{1a}$ being F, or hydrogen or Cl in the case of $X^{1a}$ being Cl; $Y^{1b}$ is hydrogen or F; $Y^{2b}$ is Br, Cl, F or methyl; $Y^{3a}$ is hydrogen, Cl, F or methyl; and $Z'$ is F or Cl.

8. A compound of the formula:

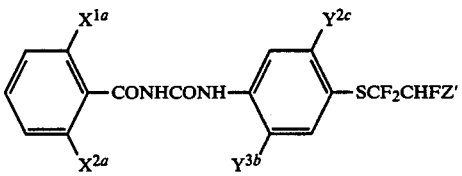

wherein $X^{1a}$ is F or Cl; $X^{2a}$ is F or Cl in the case of $X^{1a}$ being F, or hydrogen or Cl in the case of $X^{1a}$ being Cl; $Y^{2c}$ is Br, Cl or F; $Y^{3b}$ is F or Cl; and $Z'$ is F or Cl.

9. An insecticidal and/or ovicidal composition which contains a compound according to claim 1, 2, 3, 4, 5, 6, 7 or 8, together with a suitable carrier or carriers.

* * * * *